United States Patent [19]

Williams

[11] Patent Number: Plant 5,272

[45] Date of Patent: Aug. 14, 1984

[54] MINIATURE ROSE PLANT-WILSMA VARIETY

[75] Inventor: J. Benjamin Williams, Silver Spring, Md.

[73] Assignee: The Conard-Pyle Company, West Grove, Pa.

[21] Appl. No.: 393,863

[22] Filed: Jun. 30, 1982

[51] Int. Cl.[3] ..... AO1H 5/00

[52] U.S. Cl. ..... Plt./9

[58] Field of Search ..... Plt./7, 9

*Primary Examiner*—Robert E. Bagwill

*Attorney, Agent, or Firm*—Burns, Doane, Swecker & Mathis

[57] ABSTRACT

A new and distinct variety of Miniature rose plant is provided having attractive and very abundant blossoms which are Spinel red in coloration. The new variety resulted from the crossing of the Pinafore variety (U.S. Plant Pat. No. 1,810) and the unnamed seedling resulting from the cross of the Lilibet variety (U.S. Plant Pat. No. 1,209) and the Fairy Queen variety (non-patented). It is a very vigorous grower with a low-growing semi-spreading habit. The blossoms are single and petite and are borne in clusters of up to a dozen or more. The new variety is particularly suited for ornamental use in the home landscape.

1 Drawing Figure

SUMMARY OF THE INVENTION

The object of the present invention is to provide a new variety of rose plant of the Miniature Class which is distinguished from prior varieties by the following combination of characteristics:

(a) from the physical standpoint the plant with light green wood has a semi-spreading growth habit, forms abundant shiny leaves, and forms very abundant single flowers which are Spinel red in coloration; and (b) from the biological standpoint the plant has vigorous, low growing and regular vegetation, exhibits abundant and repeated florescence, and forms petals which detach cleanly.

The single nature of the blossoms gives them a pink dogwood-like appearance.

In view of these characteristics the new variety meets the needs of the horticultural industry and is particularly suited for ornamental use in the home landscape.

The new variety resulted from artificial pollination with the variety Pinafore (U.S. Plant Pat. No. 1,810) serving as seed parent, and an unnamed seedling as pollen parent which resulted from the crossing of the variety Lilibet (U.S. Plant Pat. No. 1,209) and the variety Fairy Queen (non-patented).

The characteristics and properties of this new variety have been found to be transmissible by vegetative propagation through softwood cuttings, grafting and budding performed at West Grove, Pa.

The rose plant of the new variety has been named the Wilsma variety. Plants of the new variety presently are being marketed by the Conard-Pyle Co. of West Grove, Pa., under the ASTRA trademark and are members of a family of Miniature rose plants which presently are being marketed by such company under the MINI-FLORA trademark.

BRIEF DESCRIPTION OF THE PHOTOGRAPH

The accompanying photograph shows as nearly true as it is possible to make the same in a color illustration of this character, typical specimens of plant parts from two year old plants produced from softwood cuttings and growing on their own roots in the open air during mid-June at West Grove, Pa.

In the left portion of the photograph is shown a specimen of foliage and clusters of buds wherein the sepals have opened on some of the buds, and the upper and lower surfaces of the leaflets are visible.

In the upper center and upper right portions of the photograph are shown fully opened blossoms and a bud.

In the far right portion of the photograph is shown a segment of branch.

In the lower right center of the photograph are shown two leaves of five leaflets each.

DETAILED DESCRIPTION

The plants described were grown outside during June at West Grove, Pa.

The chart utilized in the identification of the colors is that of The Royal Horticultural Society (R.H.S. Colour Chart).

Class: Miniature.

Plant:

*Height.*—Approximately 25 to 40 cm. on average.

*Bearing.*—Semi-spreading.

Branches:

*Color.*—Young stems: light green with maroon cast, Yellow-Green Group 146D and Greyed-Purple Group 187C. Mature wood: light green, Yellow-Green Group 146B.

*Thorns.*—Shape of upper edge: straight to slightly convex. Shape of lower edge: straight to slightly concave. Size: medium to large. Quantity: heavy. Color on young stems: reddish. Color on mature stems: light red, fading to straw.

Foliage:

*Stipules.*—Adnate, pectinate, narrow and linear, teeth reddish.

*Petiole.*—Inner surface: smooth, pale green, tomentose, with prickles along edge. Outer surface: light green with reddish hooked prickles.

*Leaflets.*—Number: 3 or 5 (most common), and occasionally 7. Shape: elliptical, rounded base and average summit, commonly approximately 2 cm. in length and approximately 1.25 cm. in width. Teeth: serrulate and regular.

*Color.*—Young leaves: Upper surface: medium green, Green Group 137B. Lower surface: light green, Green Group 138B. Mature leaves: Upper surface: dark green, Green Group 137A. Lower surface: medium green, slightly lighter than Green Group 137D.

Flowers:

*Number of flowers.*—Commonly 12 to 15 flowers per cluster.

*Peduncle.*—Short, straight, often pale red tint, glandular with prickles, approximately 1 to 2 cm. in length on average.

Sepals.—Inner surface: tomentose, light green, red edging on first opening. Outer surface: light green, reddish cast around mid-rib, many reddish prickles, edges often spurred.

*Buds.*—Shape: ovoid, prominent neck. Length: approximately 1 to 1.5 cm. on averge when sepals break. Size: small.

*Flower.*—Shape: solitary. Diameter: approximately 3 to 4 cm. on average. Color when sepals open: at petal apex Red Group 53D becoming Red Group 56B at center of petal to Yellow Group 4B at point of attachment. Color when fully open: at petal apex Red-Purple Group 57D becoming Red Group 56B at center of petal to Yellow Group 4B at point of attachment. Color prior to petal drop: at petal apex Red Group 55B becoming Red Group 56B at center of petal to Yellow Group 2D at point of attachment. Fragrance: very slight. Lasting quality: commonly one day. Texture: soft. Petal shape: obovate, sometimes obcordate, claw is Naples yellow, Yellow Group 11B. Number of petals: 5, which clean well. Stamens: approximately 108 on average, anthers are ochre colored, normal, heavy pollen producer. Pistils: approximately 15 on average, stigma is normal and yellowish, and styles are twisted and whitish with a fuchsia cast. Receptacle: narrow and funnel shaped.

Development:

*Vegetation.*—Vigorous and regular.

*Flowering.*—Prolific and repeated.

*Capacity of bearing fruit.*—Excellent.

*Resistance to frost.*—Normal for class.

*Resistance to diseases.*—A little better than average.

I claim:

1. A new and distinct variety of Miniature rose plant, substantially as illustrated and described, wherein:

(a) from the physical standpoint the plant with light green wood has a semi-spreading growth habit, forms abundant shiny leaves, and forms very abundant single flowers which are Spinel red in coloration; and (b) from the biological standpoint the plant has vigorous, low growing and regular vegetation, exhibits an abundant and repeated florescence, and forms petals which detach cleanly.

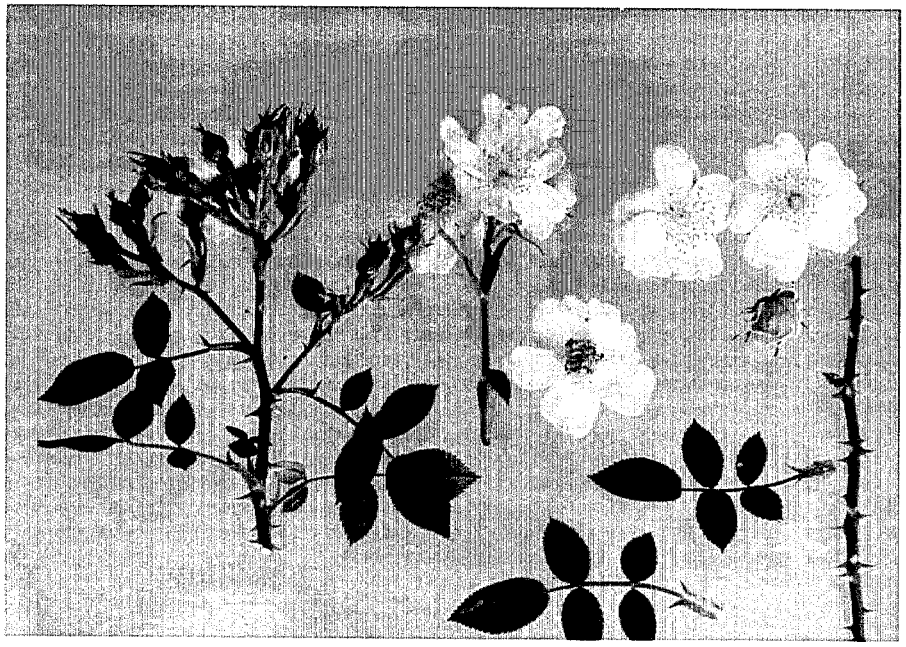

* * * * *